United States Patent
Iezzi et al.

(10) Patent No.: US 6,362,385 B1
(45) Date of Patent: *Mar. 26, 2002

(54) PROCESS FOR OBTAINING LIGHT OLEFINS BY THE DEHYDROGENATION OF THE CORRESPONDING PARAFFINS

(75) Inventors: Rodolfo Iezzi; Andrea Bartolini; Franco Buonomo, all of Milan (IT); Gueorgui Kotelnikov; Vladimir Bespalov, both of Yaroslavl (RU)

(73) Assignees: Siamprogetti S.p.A., San Donato Milanese (IT); Oao Nil Yarsintez, Yaroslavil (RU)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/120,884

(22) Filed: Jul. 23, 1998

(30) Foreign Application Priority Data

Jul. 29, 1997 (IT) .......................................... MI97A01807

(51) Int. Cl.⁷ .......................... C07C 5/333; C07C 5/373; C07C 5/327
(52) U.S. Cl. ........................ 585/661; 585/662; 585/654; 585/663
(58) Field of Search ................................. 585/661, 662, 585/654, 663; 502/232, 349, 238, 352, 239, 355, 242, 243, 235, 236, 254, 256, 263, 310, 305, 317, 319, 320, 323, 344

(56) References Cited

U.S. PATENT DOCUMENTS

| | | | | |
|---|---|---|---|---|
| 2,991,255 A | | 7/1961 | Malley et al. | 252/455 |
| 3,647,909 A | * | 3/1972 | Michaels | 585/662 |
| 3,692,863 A | * | 9/1972 | Kmecak et al. | 585/662 |
| 4,038,215 A | | 7/1977 | Manning | 252/465 |
| 5,143,886 A | | 9/1992 | Iezzi et al. | 502/242 |
| 5,258,567 A | | 11/1993 | Kerby et al. | 585/654 |
| 5,308,822 A | | 5/1994 | Iezzi et al. | 502/243 |
| 5,414,182 A | | 5/1995 | Iezzi et al. | 585/661 |
| 5,633,421 A | | 5/1997 | Iezzi et al. | 585/634 |

FOREIGN PATENT DOCUMENTS

| | | |
|---|---|---|
| FR | 2197833 | 3/1974 |
| GB | 2162082 | 1/1986 |
| WO | WO 90/06907 | 6/1990 |

* cited by examiner

Primary Examiner—Thuan D. Dang
(74) Attorney, Agent, or Firm—Oblon, Spivak, McClelland, Maier & Neustadt, P.C.

(57) ABSTRACT

A process for obtaining light olefins by the dehydrogenation of corresponding paraffins, by reacting the paraffins with a catalytic system containing chromium oxide, tin oxide, at least one alkali metal oxide, and an alumina-silica carrier, and then regenerating the catalytic system in a regenerator by burning coke deposited on its surface at a temperature higher than the average temperature of the reactor.

8 Claims, 3 Drawing Sheets

PROCESS FOR OBTAINING LIGHT OLEFINS BY THE DEHYDROGENATION OF THE CORRESPONDING PARAFFINS

FIELD OF THE INVENTION

The present invention relates to a process for obtaining light olefins by the dehydrogenation of the corresponding paraffins, in particular $C_2$–$C_{20}$ (paraffins with 2 to 20 carbon atoms).

DISCUSSION OF THE BACKGROUND

Olefins are important intermediates for the production of chemicals having a wide distribution such as: polypropylene, antiknocking additives (MTBE), fuels with a high octane number, alkylated derivatives and numerous other products.

In spite of the growing demand for these derivatives, the expansion of industrial processes for their preparation is often limited by the restricted availability of olefins, for example isobutene in the production of MTBE.

This has led to identifying other sources of olefin supply, together with the traditional ones (FCC, Cracker). Among these the source which is becoming more and more important is represented by the dehydrogenation reaction of light paraffins. This, although simple from a stoichiometric point of view, has problems with respect to thermodynamics and kinetics. The reaction is endothermal and is regulated by thermodynamic equilibrium; this leads to the necessity for temperatures higher than 500° C. for dehydrogenating $C_2$–$C_4$ paraffins with economically acceptable conversions per passage. In addition it is necessary to supply the system with heat because of the endothermal nature of the reaction.

In spite of the high operating temperatures the dehydrogenation rate is low and it is consequently necessary to operate in the presence of a suitable catalyst. The latter must be thermally stable and capable of guaranteeing high selectivities towards the desired olefin, minimizing isomerization, cracking, coking and aromatization side-reactions and ensuring industrially useful conversion values.

The inevitable formation of coke on the catalyst causes a progressive reduction in the catalytic activity and it is therefore indispensable to carry out periodic regenerations.

As a result the formulate must have a high stability under the conditions to which it is subjected during the reaction and regeneration phases.

Several efforts have been made to identify catalytic compositions which can satisfy the demands imposed by the type of process.

Patent literature in fact, cites several catalytic compositions based on noble metals and combined with other chemical species (U.S. Pat. No. 3,531,543, U.S. Pat. No. 4,786,625; U.S. Pat. No. 4,886,928; EP-351067) and also based on metal oxides in the presence of promoters, in most cases consisting of supported $Cr_2O_3$ (U.S. Pat. NO. 2,945,823; U.S. Pat. No. 2,956,030; U.S. Pat. No. 2,991,255; GB-2162082).

Both groups of formulations, however, have disadvantages: those based on noble metals require particular treatment in the regeneration phase (U.S. Pat. No. 4,438,288) to preserve the dehydrogenating activity of the metallic species, resorting for example to post-treatment with chlorinated substances and subsequent reducing treatment; those based on chromium oxide, supported on alumina, silica, silica-alumina, etc., are characterized in that they have a low selectivity to olefin owing to their acid nature which causes parasite reactions such as isomerization, cracking, coking and aromatization which are typical acid catalyzed reactions.

The selectivity to olefin is increased by modifying the formulations with the addition of alkaline and/or earth-alkaline metal oxides to mitigate the acid properties.

Literature discloses (J. Phys. Chem., Vol. 66, 1962) that the charging high quantities of alkaline oxides, with the aim of improving the selectivity, jeopardizes the catalytic performance of the formulates: the strong interactions with the chromium oxide suppress the dehydrogenating activity, whereas the residual chromium with an oxidation state of more than +3, which cannot be completely reduced as it is stabilized by the high alkyline charging, decreases the selectivity to the desired olefin.

SUMMARY OF THE INVENTION

We have surprisingly found that by using a particular catalytic system mainly consisting of $Cr_2O_3$, supported on an alumina modified with silica, to which tin oxide is added, the selectivity to the desired olefin is significantly improved.

The addition of tin drastically reduces the formation of products deriving from acid catalyzed side-reactions with a beneficial effect on the selectivity to olefin.

The process for obtaining light olefins by the dehydrogenation of the corresponding paraffins, object of the present invention, consists:

a) in reacting in a reactor, operating at a temperature of between 450 and 800° C., at a pressure of between 0.1 and 3 Atm absolute and with a GHSV space velocity of between 100 and 10000 $h^{-1}$, said paraffins with a catalytic system containing chromium oxide, tin oxide, at least one alkaline metal oxide (M) and an alumina carrier, in delta or theta phase or in mixed delta+theta or theta+alpha or delta+theta+alpha phases, modified with silica, in which:

the chromium, expressed as $Cr_2O_3$, is in a quantity of between 6 and 30% by weight, preferably between 13 and 25%;

the tin, expressed as SnO, is in a quantity of between 0.1 and 3.5% by weight, preferably between 0.2 and 2.8%;

the alkaline metal, expressed as $M_2O$, is in a quantity of between 0.4 and 3% by weight, preferably between 0.5 and 2.5;

the silica is in a quantity of between 0.08 and 3% by weight, the complement to 100 being alumina, in regenerating said catalytic system in a regenerator by burning the coke deposited on its surface operating at a temperature of more than 400° C.

The alkaline metal, preferably potassium, is used for mitigating the acid properties of the formulate to reduce secondary reactions such as, for example, cracking, coking, aromatizations and skeletal isomerizations and of bond.

With respect to the surface area of the carrier, this is preferably less than 150 $m^2/g$, determined with the BET method.

The process for preparing the catalytic system described above essentially consists in dispersing a compound of chromium, alkaline metal and tin on a carrier consisting of alumina (in delta or theta phase or mixed delta÷theta or theta+alpha or delta÷theta+alpha phases) and silica.

Below are some of the dispersion procedures of the chromium, potassium and tin oxide (stannous and/or stannic) on the carrier, it being understood that the invention is not limited to these.

This dispersion treatment can consist in the impregnation of said carrier with a solution containing the chromium, potassium and tin oxide precursors, followed by drying and calcination, or by ionic absorption, followed by the separation of the liquid and drying and calcination of the solid. Among the procedures listed above the preferred is impregnation, according to the "incipient wetness" method of the carrier with the solution containing all the precursors of the active principles.

With respect to tin, other procedures are listed with which it can be added to the catalytic system:

addition of tin to the carrier before the dispersion of the chromium and potassium oxide precursors:

treatment of the solid containing chromium and potassium oxide by ion exchange, impregnation, etc., with a solution containing a tin compound;

deposition of the tin by vapor deposition onto the carrier, before the addition of the chromium and potassium oxide precursors, using a volatile compound of the species to be deposited;

deposition of the tin by vapor deposition onto the solid containing: alumina, chromium oxide and potassium oxide, using a volatile compound of the species to be deposited.

Among the above procedures those preferred are coimpregnation of the carrier with the solution containing the precursors of the active principles: chromium, potassium and tin oxide and vapor deposition of the tin.

Both inorganic and organic salts of tin, or organometallic derivatives can be used as precursors of stannous and/or stannic oxide.

Inorganic or organic salts, not very soluble in water, can be used, after controlling the pH of the solution which is influenced by the their solubility.

Organometallic derivatives are used adopting organic solvents in which they are dissolved to be added to the catalytic system according to the procedures described above.

The regeneration is carried out in air and/or oxygen, possibly increasing the temperature of the catalytic system itself to suitable values, for example by the combustion of an appropriate fuel. This regeneration must be followed by the reduction phase of the catalyst to reduce the hexavalent chromium formed during the regeneration phase.

The process claimed can be applied to any dehydrogenation technology whether this be fixed bed, fluid or mobile.

The process can be preferably carried out in a fluid bed system essentially consisting of a reactor in which the dehydrogenation reaction takes place and a regenerator in which the catalyst is regenerated for combustion of the coke deposited there during the reaction phase.

In the reactor-regenerator system, the catalyst in its fluidized state circulates continuously between reactor and regenerator, allowing the process to operate in continuous and the heat necessary for the reaction is supplied by the regenerated catalyst, which reaches the reactor at a temperature which is higher than the average reaction temperature.

The catalyst is maintained in its fluidized state in the reactor by the reagent gas which enters the catalytic bed from below, through a specific distribution system.

The reacted gas leaves the reactor from above, after passing through a system of cyclones or another suitable separation system of the powders; it can subsequently be sent to a heat exchanger to preheat the feeding and then to the separation section where the olefin produced is recovered, whereas the non-reacted paraffin can be recycled to the synthesis, and the by-products are separated and can also be used in the regenerator as fuel gas.

When there is an etherification plant downstream of the dehydrogenation, the separation section serves only to eliminate the by-products.

In the reactor, the catalyst in its fluidized state, moves in countercurrent with respect to the gas phase: it enters the catalytic bed from above, through a distributor which distributes it equally onto the surface of the bed and it leaves the reactor from below, passing by gravity into a desorption zone, which is part of the reactor, with a diameter less than or equal to the reaction zone, where the interparticle gas is shifted and desorbed, by introducing nitrogen or methane from below, so that the shifted or desorbed gas re-enters the reactor avoiding losses in reagents or products.

The catalyst, still in its fluidized state, is subsequently sent, pneumatically, to the regenerator.

In the fluid bed reactor, it is preferable to operate:

at a temperature maintained, by acting on the flow rate of the regenerated catalyst, of between 450 and 650° C., depending on the paraffin or mixture of paraffins treated;

at a pressure which is atmospheric or slightly higher;

at a space velocity of between 100 and 1000 $h^{-1}$ ((Nlitre of gas per hour and per litre of catalyst), more preferably between 150 and 200;

with a residence time of the catalyst varying in the fluid bed zone from 5 to 30 minutes, more preferably between 10 and 15 minutes, in the desorption zone from 0.2 to 10 minutes.

Grids with a free area of between 10 and 90%, preferably between 20 and 40%, can be horizontally arranged inside the reactor, at a distance of between 20 and 200 cm from each other.

The purpose of these grids is to prevent gas and solid from remixing, so that the flow of gas inside the reactor looks like a plug flow: in this way the conversion of the paraffin and selectivity to the desired olefin are maximized.

In particular the selectivity can be further maximized by the axial thermal profile which is established along the bed with the maximum temperature in the upper part where the regenerated catalyst arrives and the minimum temperature in the lower part: the difference in temperature along the bed is preferably between 15 and 65° C.

In order to optimize the axial thermal profile, it is also possible to distribute the regenerated catalyst at varying heights in the catalytic bed. The pneumatic transport system from the reactor to the regenerator consists of a transport line with at least one zone in which the catalyst has a downward movement, preferably maintained under intermediate conditions between the minimum fluidization and minimum bubble formation, by the entry of suitable quantities of gas at appropriate heights and a zone in which the catalyst moves with an upward movement until it reaches the upper part of the catalytic bed of the regenerator, by the entry of gas at the base which considerably decreases the density of the emulsion.

The regenerator preferably has dimensions which are similar to those of the reactor.

An appropriate distributor divides the catalyst coming from the reactor onto the surface of the catalytic bed. The regeneration takes place inside the bed by the combustion of coke deposited on the catalyst and the heating of the catalyst by the combustion of methane or fuel gas with air or oxygen or another fuel gas, at a temperature which is higher than the average temperature of the reactor.

Before being sent to the reactor the regenerated catalyst is subjected to reducing treatment, at temperatures of between 650 and 680° C. and for a time of between 0.2 and 10 minutes, to eliminate the hexavalent chromium, it is then desorbed of the combustion and reduction products.

Also in the regenerator, the movement of the gas and solid takes place in countercurrent: air is admitted to the bottom of the catalytic bed whereas fuel gas enters at suitable heights along the bed.

The gas leaving the regenerator, consisting of nitrogen and combustion products can pass through cyclones, or another system, situated in the upper part of the apparatus, to separate the accumulated powders, and subsequently, after leaving the regenerator, it can be sent to a heat exchanger for the preheating of the combustion air.

Before being discharged into the atmosphere, these gases can pass through a filter system or other devices for reducing the powder content to a few tens of mg per $Nm^3$ of gas.

As the combustion catalytically takes place at a temperature which is lower than 700° C., the content of carbon monoxide and nitrogen oxides in the discharge gas is such as not to require further purification treatment.

In the regenerator it is preferable to operate at a pressure which is either atmospheric or slightly higher, at a space velocity of between 100 and 1000 $h^{-1}$ and with a residence time of the solid, varying from 5 to 60 minutes, more preferably between 20 and 40 minutes.

The regenerated catalyst is transported to the reactor in the same way that the exhausted catalyst is transported to the regenerator.

The reactor-regenerator system thus conceived allows the operating parameters and performance for the whole technical life of the plant to be kept constant.

Aliquots of catalyst are periodically discharged from the system and substituted with equal aliquots of fresh catalyst, but without having to interrupt the functioning of the plant.

The advantages of the use of a fluid bed reactor-regenerator system can be synthesized as follows:

- the optimum temperature profile in the reactor allows the yield to olefin to be maximized;
- the heat is directly transferred to the reaction by the regenerated catalyst: there are no thermal exchange surfaces and the strong remixing of the fluid bed prevents the formation of high temperature points which would lower the selectivity;
- the fluid bed process does not require recycles of hydrogen which are harmful from a thermo-dynamic point of view, but necessary in other configurations for keeping the temperature under control;
- all the other operations take place in continuous and it is not necessary to modify the operating parameters during the whole life of the plant;
- the plant can operate with wide flexibility in terms of present productive capacity with respect to the project capacity;
- the reaction and regeneration take place in physically separated zones and there cannot be any mixing of hydrocarbon streams with streams containing oxygen;
- the process is carried out at atmospheric or a slightly higher pressure: there is therefore no possibility of external infiltrations of air into the reaction zone;
- no particular treatment is necessary for reducing the emissions of gaseous pollutants.

Figure 1:
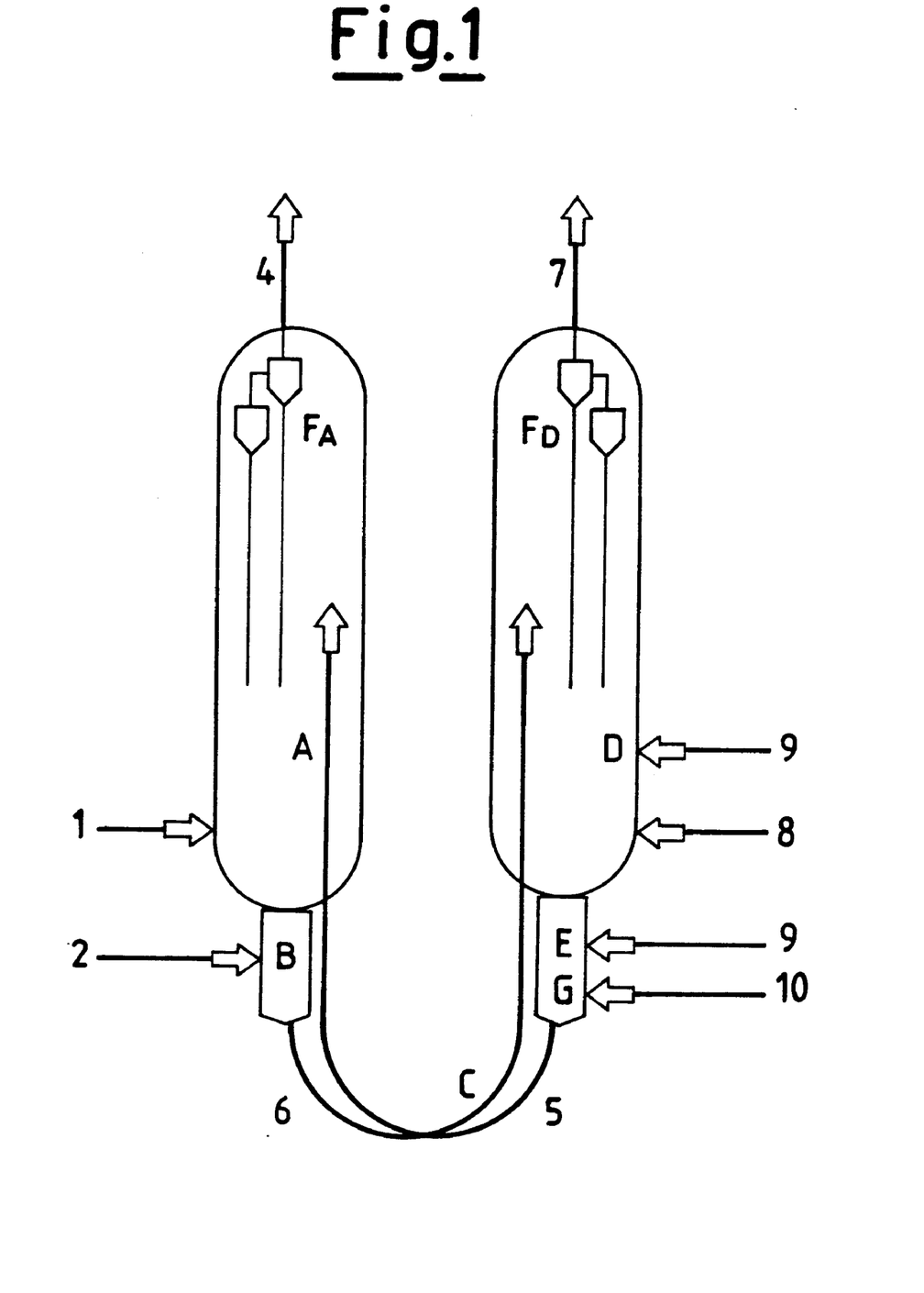
FIG. 1 shows an apparatus for carrying out the presently-disclosed process.

FIG. 1 shows a possible application of the reactor-regenerator scheme described above.

The hydrocarbon feeding (1) enters the reactor (A) through a suitable distributor (not shown in the figure), whereas the gases after the reaction leave the reactor from line (4) after passing through the cyclones $F_A$.

The regenerated catalyst (5) arrives at the top of the catalytic bed and leaves the reactor (A) passing into the desorber (B), where it enters into contact with the desorbing gas (2). The catalyst subsequently enters the transport line (6), in which it is sent to the regenerator (D), and precisely to the upper part of the catalytic bed.

In this case a single line of gas entry along the transport line, is shown (6). The transport line in this application is characterized in that it has a U-shaped connection between the downward and upward part. The catalyst descends along the regenerator (D), enters the reducer, then the desorber (G) and finally the transport line (C) and is sent to the reactor. The regenerator air enters (8), the combustion gas (9), which is the same gas used for the reduction of the catalyst in (E), and the desorbing gas (10), again through suitable distributors (not shown in the figure).

The gases, after passing through the cyclones $F_O$, leave via (7).

Several examples are provided which should not be considered as limiting the present invention.

EXAMPLE 1

Comparative

A microspheroidal pseudobohemite is prepared to which silica has been added (1.2% w), with a particle diameter of between 5÷300 microns, by spray-drying a hydrated alumina sol and Ludox silica.

A sample of the pseudobohemite is subjected to thermal treatment consisting in a first calcination at 450° C. for an hour, followed by another at 1030° C. for 4 hours in a stream of dry air.

Figure 2:
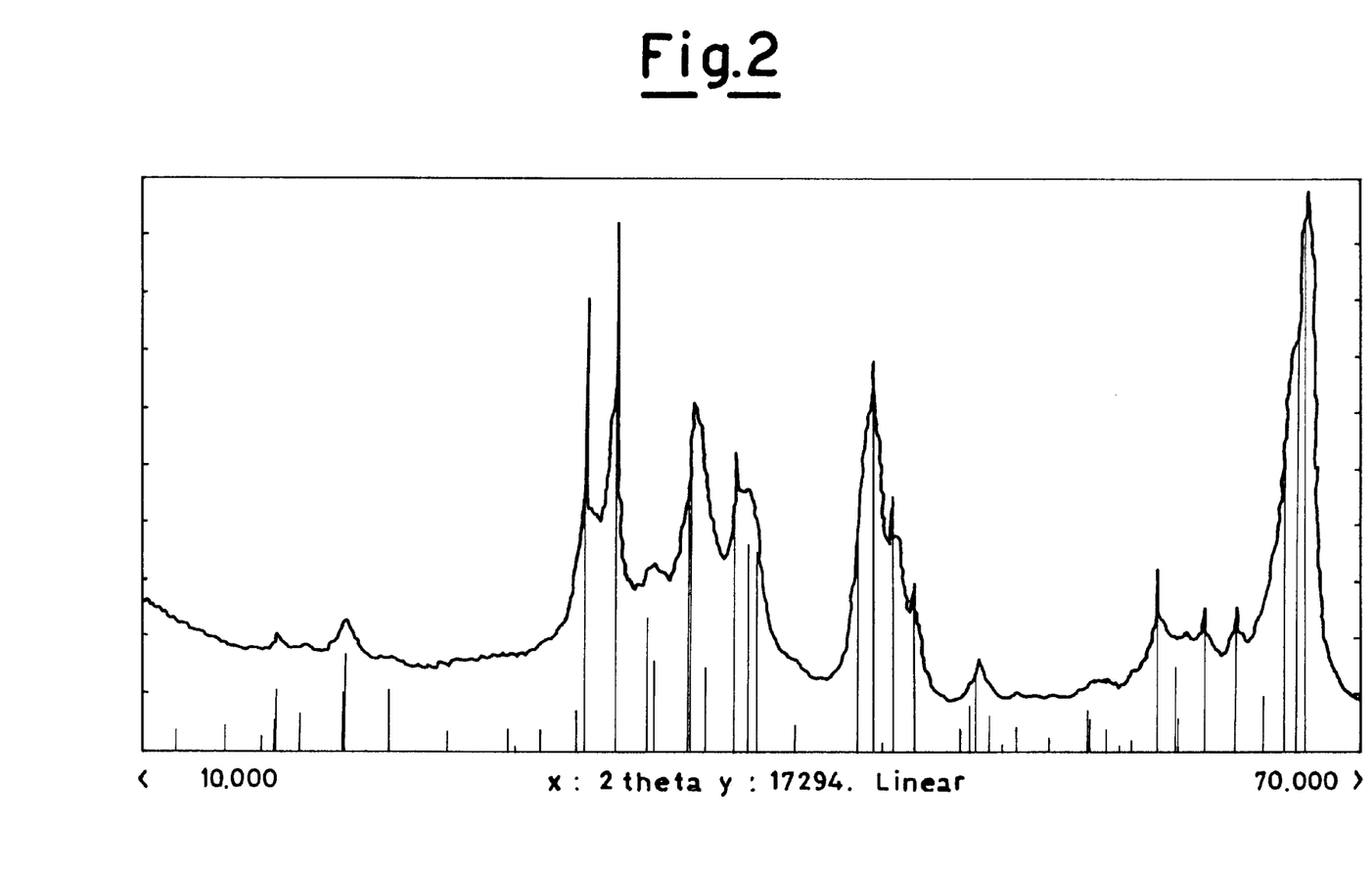
FIG. 2 is an XRD spectrum of a product described in (Comparative) Example 1.

The product obtained has a specific surface of 100 $m^2/g$, a porosity of 0.34 cc/g and essentially consists of delta and theta transition aluminas, accompanied by a small quantity of alpha alumina (See the XRD spectrum in FIG. 2).

200 g of this alumina were impregnated, using the incipient wetness procedure, with 68 cc of an aqueous solution containing 67.5 gr of $CrO_3$ (99.8% w) and 6.4 g of KOH (90% w) in deionized water, maintained at a temperature of 85° C. The impregnated product was left to rest for an hour at room temperature and subsequently dried at 90° C. for 15 hours. The dried product was finally activated, in a stream of dry air, at 750° C. for 4 hours.

The weight composition of the formulate proved to be as follows:

20% $Cr_2O_3$, 1.89% $K_2O$, 1.25% $SiO_2$, $Al_2O_3$ the complement to 100.

The catalytic performances in the dehydrogenation reaction of isobutane, measured in the temperature range of between 540÷580° C. with the procedure already described, are shown in table 1.

EXAMPLE 2

200 g of microspheroidal alumina, prepared as described in example 1, are impregnated according to the method described above with 68 cc of an aqueous solution containing: 68.3 g of $CrO_3$ (99.8% w), 6.48 g of KOH (90% w) and 4.13 g of $SnC_2O_4$ (99.9% w) in deionized water, maintained at the same temperature as example 1.

The impregnated product is treated as described in the above example to give a catalyst whose weight composition proves to be the following: 20% $Cr_2O_3$, 1.89% $K_2O$, 0.9% SnO, 1.23% $SiO_2$, $Al_2O_3$ the complement to 100.

The catalytic performances in the dehydrogenation reaction of isobutane are shown in table 1.

EXAMPLE 3

200 g of microspheroidal alumina, prepared as described in example 1, are impregnated according to the method described above with 68 cc of an aqueous solution containing: 68.8 g of $CrO_3$ (99.8% w), 6.52 g of KOH (90% w) and 5.61 g of $SnC_2O_4$ (99.9% w) in deionized water, maintained at the same temperature as example 1.

The impregnated product is treated as described in the above example to give a catalyst having the following weight composition: 20% $Cr_2O_3$, 1.89% $K_2O$, 1.4% SnO, 1.22% $SiO_2$, $Al_2O_3$ the complement to 100.

The catalytic performances in the dehydrogenation reaction of isobutane are shown in table 1.

EXAMPLE 4

200 g of microspheroidal alumina, prepared as described in example 1, are impregnated according to the method described above with 68 cc of an aqueous solution containing: 67.9 g of $CrO_3$ (99.8% w), 6.44 g of KOH (90% w) and 1.78 g of $SnC_2O_4$ (99.9% w) in deionized water, maintained at the same temperature as example 1.

The impregnated product is treated as described in the above example to give a catalyst with the following weight composition: 20% $Cr_2O_3$, 1.89% $K_2O$, 0.45% SnO, 1.22% $SiO_2$, $Al_2O_3$ the complement to 100.

The catalytic performances in the dehydrogenation reaction of isobutane are shown in table 1.

EXAMPLE 5

200 g of microspheroidal alumina, prepared as described in example 1, are impregnated according to the method described above with 68 cc of an aqueous solution containing: 67.7 g of $CrO_3$ (99.8% w), 6.42 g of KOH (90% w) and 0.91 g of $SnC_2O_4$ (99.9% w), maintained at the same temperature as example 1.

The impregnated product is treated as described in the above example to give a catalyst with the following weight composition: 20% $Cr_2O_3$, 1.89% $K_2O$, 0.23% SnO, 1.25% $SiO_2$, $Al_2O_3$ the complement to 100.

The catalytic performances in the dehydrogenation reaction of isobutane are shown in table 1.

EXAMPLE 6

200 g of microspheroidal alumina, prepared as described in example 1, were impregnated, with the incipient wetness procedure, with 44 cc of a methanol solution containing 3.99 g of dissolved tin dimethoxy dibutyl $(CH_3O)_2(Sn(C_4H_9)_2$, in a nitrogen atmosphere. The impregnated product was left to rest for 1 hour at room temperature and subsequently dried at 90° C. until the complete removal of the methanol.

The dried product was finally calcined at 750° C. for 4 hours, in an atmosphere of dry air.

The weight composition of the formulate proved to be the following: 20% $Cr_2O_3$, 1.89% $K_2O$, 0.87% SnO, 1.23% $SiO_2$, $Al_2O_3$ the complement to 100.

The catalytic performances of the formulate in the dehydrogenation reaction of isobutane are shown in table 1.

EXAMPLE 7

200 g of the same catalyst used in example 6 were modified with tin using the vapor deposition technique. For this purpose the sample of catalyst was charged into a quartz reactor equipped with a thermometer holder and ceramic distributor with calibrated porosity to obtain the homogeneous distribution of the nitrogen at the bottom of the bed. The reactor with the material was placed in an electric oven, with partialized heating, and nitrogen was fed (40÷45 Nl/h) through the porous distributor, which maintained the fluidization of the material. When the preset temperature of 200° C. for the deposition of the tin had been reached, the longitudinal thermal profile of the bed was carried out before feeding the tin precursor.

Once it had been asserted that the temperature of the bed was homogeneous within ±1° C. with respect to the preset temperature, 10÷15 Nl/h of nitrogen saturated with Tin Dimethoxy Dibutyl $(Ch_3O)_2Sn(C_4H_9)_2$ were introduced, at a temperature of between 150÷170° C., into the catalytic bed. The saturated stream was fed from the top of the reactor which through the quartz tube, passing into the catalytic bed and porous distributor, was mixed downstream of the septum with the fluidization nitrogen. The flow leaving the reactor was cooled to recover the non-reacted tin Dimethoxy Dibutyl.

The quantity of tin was dosed by monitoring the weight of the residual precursor in the saturator.

When the required quantity of precursor for obtaining the theoretical loading of tin had been removed, the operation was interrupted.

The temperature of the catalytic bed was increased until it reached 750° C., and maintained for 4 hours to carry out the activation of the material. The activated product was analyzed to determine the weight composition which proved to be the following: 20% $Cr_2O_3$, 1.89% $K_2O$, 0.33% SnO, 1.24% $SiO_2$, $Al_2O_3$ the complement to 100.

The performances of the formulate in the dehydrogenation reaction of isobutane are shown in table 1.

EXAMPLE 8

Comparative

Figure 3:
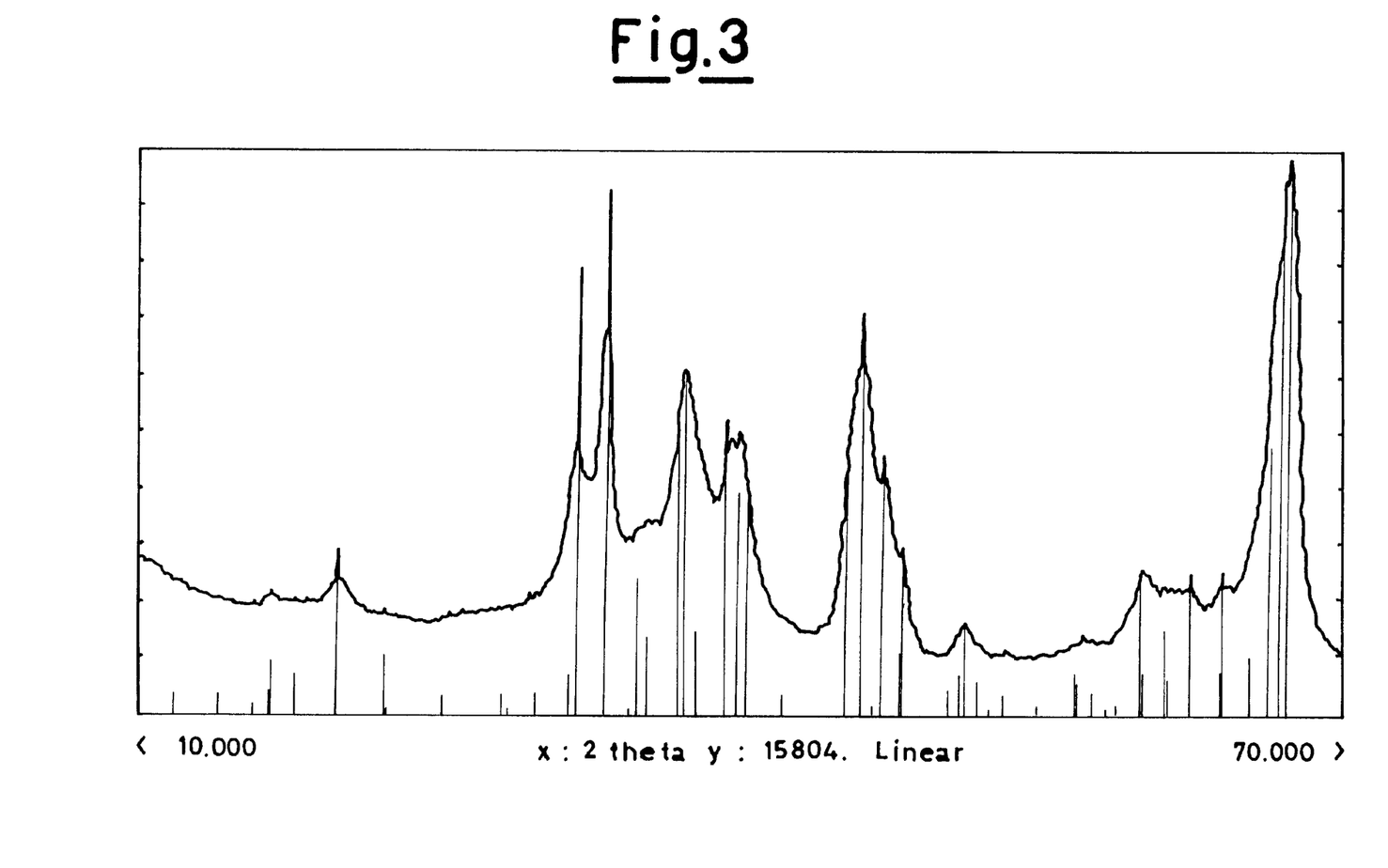
FIG. 3 is an XRD spectrum of a product described in (Comparative) Example 8.

A 1000 g sample of the pseudobohemite prepared according to the procedure described in example 1, was subjected to thermal treatment consisting in a first calcination at 450° C. for an hour, followed by another at 1000° C. for 4 hours, in a stream of dry air. The calcined product has a surface area of 130 m²/g, a porosity of 0.49 cc/g and consists of delta and thetas transition aluminas (See the XRD spectrum in FIG. 3).

150 g of this alumina were impregnated, using the incipient wetness procedure, with 74 cc of an aqueous solution containing 66.8 g of $CrO_3$ (99.8% w) and 5.36 g of potassium carbonate (45% w/w of KOH) and maintained at the same temperature as example 1. The impregnated product was left to rest for an hour at room temperature and subsequently dried at 90° C. for 15 hours. The dried product was finally activated, in a stream of dry air, at 750° C. for 4 hours. The weight composition of the formulate proved to be as follows:

25% $Cr_2O_3$, 1% $K_2O$, 1.18% $SiO_2$, $Al_2O_3$ the complement to 100. This formulate was tested in the dehydrogenation reaction of propane, within the range 560÷600° C., obtaining the performances indicated in table 2.

EXAMPLE 9

150 g of the same alumina used in example 8 were impregnated with 74 cc of a methanol solution containing 3.75 g of Tin Dimethoxy-Dibutyl $(CH_3O)_2Sn(C_4H_9)_2$, with the incipient wetness procedure.

The impregnated product was left to rest for an hour and subsequently dried at 90° C. until the complete removal of the methanol. The dried product was finally calcined at 600° C. for 2 hours, in a stream of dry air. The calcined product was impregnated, according to the method described in example 8, with 74 cc of an aqueous solution containing 67.6 g of $CrO_3$ (99.8% w/w) and 5.42 g of potassium carbonate (45% solution w/w of KOH), at the same temperature as example 1, to obtain a catalyst with the following weight composition: 25% $Cr_2O_3$, 1% $K_2O$, 0.84% SnO, 1.18% $SiO_2$, $Al_2O_3$ the complement to 100. The catalytic performances in the dehydrogenation reaction of propane are indicated in table 2.

EXAMPLE 10

150 g of the same alumina used in example 9 were impregnated with 74 cc of a methanol solution containing 7.63 g of Tin Dimethoxy-Dibutyl $(CH_3O)_2Sn(C_4H_9)_2$, with the same procedure described in example 9. The calcined product, under the same conditions as example 9, was impregnated with 74 cc of an aqueous solution, with the same procedure as example 8, containing 68.4 g of $CrO_3$ (99.8% w/w) and 5.48 g of potassium carbonate (45% solution w/w of KOH), at the same temperature as example 1, to obtain a catalyst with the following weight composition: 25% $Cr_2O_3$, 1% $K_2O$, 1.68% SnO, 1.17% $SiO_2$, $Al_2O_3$ the complement to 100. The formulate was tested in the dehydrogenation reaction of propane, obtaining the performances indicated in table 2.

EXAMPLE 11

150 g of the same alumina used in example 9 were impregnated with 74 cc of a methanol solution containing 11.61 g of Tin Dimethoxy-Dibutyl $(CH_3O)_2Sn(C_4H_9)_2$, with the same procedure described in example 9. The calcined product, under the same conditions as example 9, was impregnated with 74 cc of an aqueous solution, with the same procedure as example 8, containing 69.2 g of $CrO_3$ (99.8% w/w) and 5.55 g of potassium carbonate (45% solution w/w of KOH), at the same temperature as example 1, to obtain a catalyst with the following weight composition: 25% $Cr_2O_3$, 1% $K_2O$, 2.52% SnO, 1.14% $SiO_2$, $Al_2O_3$ the complement to 100. The catalytic performances of the formulate in the dehydrogenation reaction of propane are indicated in table 2.

EXAMPLE 12

150 g of the same alumina used in example 8 were impregnated with 74 cc of an aqueous solution, at the same temperature as example 1, in which the following products were dissolved: 68.4 g of $CrO_3$ (99.8%), 5.49 g of potassium carbonate (45% solution w/w of KOH) and 5.35 g of $SnC_2O_4$ (99.9% w/w). The drying and activation were carried out with the procedure described in example 1. The weight composition of the formulate proved to be as follows: 25% $Cr_2O_3$, 1% $K_2O$, 1.68% SnO, $Al_2O_3$ the complement to 100. The catalytic performances in the dehydrogenation of propane are indicated in table 2.

EXAMPLE 13

150 g of catalyst, prepared with the procedure described in example 8, were impregnated with 39 cc of a methanol solution containing 3.03 g of $(CH_3\!\!-\!\!O)_2Sn(C_4H_9)_2$, according to the procedure described in example 6. The formulate after activation was analyzed to determine its composition and tested in the dehydrogenation reaction of propane.

The weight composition proved to be the following: 24.8% $Cr_2O_3$, 0.99% $K_2O$, 0.91% SnO, 1.17% $SiO_2$, $Al_2O_3$ the complement to 100.

The catalytic performances are summarized in table 2.

EXAMPLE 14

235 g of catalyst are prepared with the procedure described in example 2, by the impregnation of 200 g of alumina, the same used in the same example, with 68 cc of an aqueous solution containing 37.2 g of $CrO_3$ (99.8% w), 5.87 g of KOH (90% w) and 3.26 g of $SnC_2O_4$ (99.9%), maintained at a temperature of 85° C., having the following weight composition: 12% $Cr_2O_3$, 1.36% $SiO_2$, 1.89% $K_2O$, 0.9% SnO, $Al_2O_3$ the complement to 100.

The catalyst was tested in the dehydrogenation reaction of isobutane, obtaining the performances indicated in table 1.

EXAMPLE 15

Comparative 200 g of alumina with a specific surface of 104 $m^2/g$ and a porosity of 0.34 cc/g, obtained by the calcination of a sample of pseudobohemite obtained according to the procedure described in example 1 but without silica, were impregnated with 68 cc of an aqueous solution containing 68.3 g of $CrO_3$ (99.8% w), 6.48 g of KOH (90% w) and 4.13 g of $SnC_2O_4$ (99.9%) to obtain a catalyst having the following weight composition: 20% $Cr_2O_3$, 1.89% $K_2O$, 0.9% SnO, $Al_2O_3$ the complement to 100. The formulate was tested in the dehydrogenation reaction of isobutane, obtaining the performances indicated in table 1.

EXAMPLE 16

A sample of catalyst was prepared with the same procedure and same alumina sued in example 2, having the following weight composition:

20% $Cr_2O_3$, 3% $K_2O$, 0.9% SnO, 1.22% $SiO_2$, $Al_2O_3$ the complement to 100.

The catalytic performances in the dehydrogenation reaction of isobutane are indicated in table 1.

EXAMPLE 17

A sample of catalyst was prepared with the same procedure and same alumina used in example 2, having the following weight composition:

20% $Cr_2O_3$, 0.2% $K_2O$, 0.9% SnO, 1.27% $SiO_2$, $Al_2O_3$ the complement to 100.

The catalytic performances in the dehydrogenation reaction of isobutane are indicated in table 1.

Catalytic Tests

The products prepared in example 1–17 were tested in a fluid bed using a quartz reactor equipped with a distributor with a calibrated porosity also made of quartz. An expander is placed on the head of the reactor, which has the function of decelerating the effluent allowing the fine particles to fall back into the catalytic bed. The catalytic cycle, which is such as to simulate the behaviour on an industrial reactor, consists of a reaction phase, in which the hydrocarbon is fed for a duration of 15 minutes, a stripping phase, in which nitrogen is passed to liberate the catalyst from the products adsorbed during 10 minutes, a regeneration phase, in which the regeneration gas consisting of air is fed in tests carried out for a duration of 30 minutes, a washing phase with nitrogen, for the duration of at least 10 minutes, a reduction phase in which the reducing gas consisting of methane is fed for the duration of 4 minutes to reduce the hexavalent chromium formed in the regeneration phase, a washing phase with nitrogen for at least 10 minutes followed by the reaction phase for the duration of 15 minutes. The requisites of the industrial fluid bed dehydrogenation process suggest that the regeneration be carried out at temperatures which are higher than the reaction temperature: in the catalytic tests the regeneration and reduction were carried out at 650° C., whereas the reaction was carried out within the temperature range of 560 to 600° C. in the case of dehydrogenation of propane and within the range of 540 to 580° C. in the case of dehydrogenation of isobutane.

The space velocity of the reagent has a value of 400± Nl/cat.h. In the first catalytic test each catalyst was reduced, according to the procedure already described, before carrying out the dehydrogenation reaction.

The reagent sent into the reactor is dosed by weight.

The effluent of the reactor during the reaction and stripping phases is first passed through a cold trap to stop the heavy products whose weight, carbon and hydrogen % are subsequently determined and then collected in a multilayer sampling bag having no affinity with hydrocarbons. The content of the bag is then measured with a volumetric pump and analyzed by gaschromatography.

Finally, at the end of the stripping of 10' with $N_2$, a sample of catalyst is taken to determine the quantity of coke formed. The data thus obtained are introduced into a personal computer to calculate the material balance, conversion and selectivity to the various products.

TABLE 1

ISOBUTANE DEHYDROGENATION
GHSV = (400 + −5) Nor. Lit. Iso - C4H10/h/l cat.
Fluid bed

| Example | Cr2O3 w/w % | K2O w/w % | SiO2 w/w % | SnO w/w % | Temperat. ° C. | Conversion (% iso - C4H10) | Selectivity (% mol. iso - C4H8) | Yield (% mol. iso - C4H8) |
|---|---|---|---|---|---|---|---|---|
| 1 comp. | 20 | 1.89 | 1.25 | absent | 560 | 54 | 88 | 47.5 |
| 2 | 20 | 1.89 | 1.23 | 0.90 | 570 | 54 | 94 | 50.7 |
| 3 | 20 | 1.89 | 1.22 | 1.40 | 589 | 54 | 92 | 49.7 |
| 4 | 20 | 1.89 | 1.25 | 0.45 | 565 | 54 | 91 | 49.1 |
| 5 | 20 | 1.89 | 1.25 | 0.23 | 562 | 54 | 90 | 48.6 |
| 6 | 20 | 1.89 | 1.23 | 0.87 | 575 | 54 | 92 | 49.7 |
| 7 | 20 | 1.89 | 1.24 | 0.33 | 564 | 54 | 91 | 49.1 |
| 14 | 12 | 1.89 | 1.36 | 0.90 | 573 | 54 | 90 | 48.6 |
| 15 comp. | 20 | 1.89 | absent | 0.90 | 568 | 54 | 89 | 48.1 |
| 16 | 20 | 3.0 | 1.22 | 0.9 | 570 | 54 | 87 | 46.9 |
| 17 | 20 | 0.20 | 1.27 | 0.9 | 568 | 54 | 70 | 37.8 |

TABLE 2

PROPANE DEHYDROGENATION
GHSH = (400 + −5) Nl/h/l cat.
Fluid bed

| Example | Cr2O3 w/w % | K2O w/w % | SiO2 w/w % | SnO w/w % | Temperat. ° C. | Conversion (% C3H8) | Selectivity (% mol. C3H6) | Yield (% mol. C3H6) |
|---|---|---|---|---|---|---|---|---|
| 8 comp. | 25 | 1.0 | 1.18 | absent | 566 | 37 | 78 | 28.9 |
| 9 | 25 | 1.0 | 1.18 | 0.84 | 570 | 37 | 86 | 31.8 |
| 10 | 25 | 1.0 | 1.17 | 1.68 | 580 | 37 | 88 | 32.5 |
| 11 | 25 | 1.0 | 1.14 | 2.52 | 588 | 37 | 84 | 31.1 |
| 12 | 25 | 1.0 | 1.15 | 1.68 | 582 | 37 | 87 | 32.2 |
| 13 | 24.8 | 0.99 | 1.17 | 0.91 | 590 | 37 | 89 | 32.9 |

What is claim is:

1. A process for obtaining light olefins by the dehydrogenation of the corresponding paraffins, comprising:

a) reacting said paraffins with a catalytic system in a reactor, operating at a temperature of between 450 and 800° C., at a pressure of between 0.1 and 3 Atm absolute and with a GHSV space velocity of between 100 and 10000 $h^{-1}$, wherein the catalytic system contains chromium oxide, tin oxide, at least one alkali metal oxide (M) and an alumina-silica carrier, wherein the alumina is in delta or theta phase or in mixed delta+theta or theta+alpha or delta+theta+alpha phases, wherein the chromium expressed as $Cr_2O_3$, is in a quantity of between 6 and 30% by weight;

the tin, expressed as SnO, is in a quantity of between 0.1 and 3.5% by weight;

the alkali metal, expressed as $M_2O$, is in a quantity of between 0.4 and 3% by weight;

the silica is in a quantity of between 0.08 and 3% by weight, and the remainder is alumina, b) regenerating said catalytic system in a regenerator by burning coke deposited on its surface at a temperature higher than the average temperature of the reactor.

2. The process according to claim 1 wherein:

the chromium, expressed as $Cr_2O_3$, is in a quantity of between 13 and 25% by weight;

the tin, expressed as SnO, is in a quantity of between 0.2 and 2.6% by weight;

the alkali metal, expressed as $M_2O$, is in a quantity of between 0.5 and 2.5% by weight.

3. The process, according to claim 1 wherein the alkali metal is potassium.

4. The process according to claim 1 wherein the carrier has a surface area of less than 150 $m^2/g$.

5. The process according to claim 1 wherein the reactor and regenerator are each a fluid bed.

6. The process according to claim 5 wherein the dehydrogenation is carried out at a temperature of between 450 and 650° C., at a pressure which is atmospheric or higher, at a GHSV space velocity of between 100 and 1000 $h^{-1}$ and with a residence time of the catalyst in the fluid bed varying from 5 to 30 minutes.

7. The process according to claim 6 wherein the space velocity is between 150 and 200 $h^{-1}$ and the residence time of the catalyst varies from 10 to 15 minutes.

8. The process according to claim 5 wherein the regeneration is carried out with air or oxygen or another combustion-supporting gas, at a pressure which is atmospheric or higher, at a space velocity of between 100 and 1000 $h^{-1}$ and with a residence time of the solid varying from 5 to 60 minutes.

* * * * *

UNITED STATES PATENT AND TRADEMARK OFFICE
CERTIFICATE OF CORRECTION

PATENT NO. : 6,362,385 B1
DATED : March 26, 2002
INVENTOR(S) : Iezzi et al.

It is certified that error appears in the above-identified patent and that said Letters Patent is hereby corrected as shown below:

<u>Title page,</u>
Item [73], the Assignee information is listed incorrectly. It should read as follows:
-- [73] Assignee: Snamprogetti S.p.A., San Donato Milanese (IT); Oao Nii Yarsintez, Yaroslavl (RU) --

Signed and Sealed this

Twenty-fourth Day of September, 2002

Attest:

JAMES E. ROGAN
Attesting Officer
Director of the United States Patent and Trademark Office